United States Patent [19]
Preikschat et al.

[11] Patent Number: 5,600,058
[45] Date of Patent: Feb. 4, 1997

[54] ROTATING CONSISTENCY TRANSMITTER AND METHOD

[75] Inventors: Ekhard Preikschat, Bellevue; Robert J. Hilker, Bothell, both of Wash.

[73] Assignee: APPA Systems, Inc., Bellevue, Wash.

[21] Appl. No.: 525,945

[22] Filed: Sep. 8, 1995

[51] Int. Cl.$^6$ .................................................. G01N 11/14
[52] U.S. Cl. .......................................... 73/54.32; 73/54.33
[58] Field of Search ................................ 73/54.28, 54.29, 73/54.32, 54.33, 54.34, 54.35

[56] References Cited

U.S. PATENT DOCUMENTS

| | | | |
|---|---|---|---|
| 2,519,378 | 8/1950 | Kilpatrick | 73/54.33 |
| 3,572,086 | 3/1971 | Johnston | 73/54.32 |
| 4,062,226 | 12/1977 | Hietala | 73/54.23 |
| 4,077,251 | 3/1978 | Winter | 73/54.35 |
| 4,175,425 | 11/1979 | Brookfield | 73/54.28 |
| 4,878,378 | 11/1989 | Harada | 73/54.35 |
| 5,349,848 | 9/1994 | Driver | 73/54.28 |

FOREIGN PATENT DOCUMENTS

| | | | |
|---|---|---|---|
| 2066483 | 7/1981 | United Kingdom | 73/54.33 |

*Primary Examiner*—Michael Brock
*Attorney, Agent, or Firm*—Dean A. Craine

[57] ABSTRACT

A rotating consistency transmitter and method of measuring the viscosity, consistency, concentration or the rheological properties of a flowing multi-purpose material in a pipeline by measuring the torque acting on a rotating shaft, which at one end is driven by a motor and at the other end is attached to an impeller directly positioned inside the pipeline. The rotating shaft is made up of three concentric shafts, an outer drive shaft, a middle sensor shaft and an inner reference shaft aligned and attached together so that a single motor may be used to rotate it. The sensor shaft is connected at one end to the drive shaft and connected at the opposite end to the inner reference shaft. When material is present in the main pipeline and in contact with the impeller, rotation of the impeller is impeded, thereby producing a torque across the sensor shaft. This torque causes a twisting action on the sensor shaft which may be determined by measuring the angular displacement between the outer drive shaft and the inner reference shaft. The angular displacement is measured by passing focused light beam across two optical disks, one being attached to one end of the reference shaft. The amount of light transmitted through the two optical disks is a direct measure of the torque acting on the sensor shaft which, in turn, directly relates to the drag forces acting on the impeller.

19 Claims, 5 Drawing Sheets

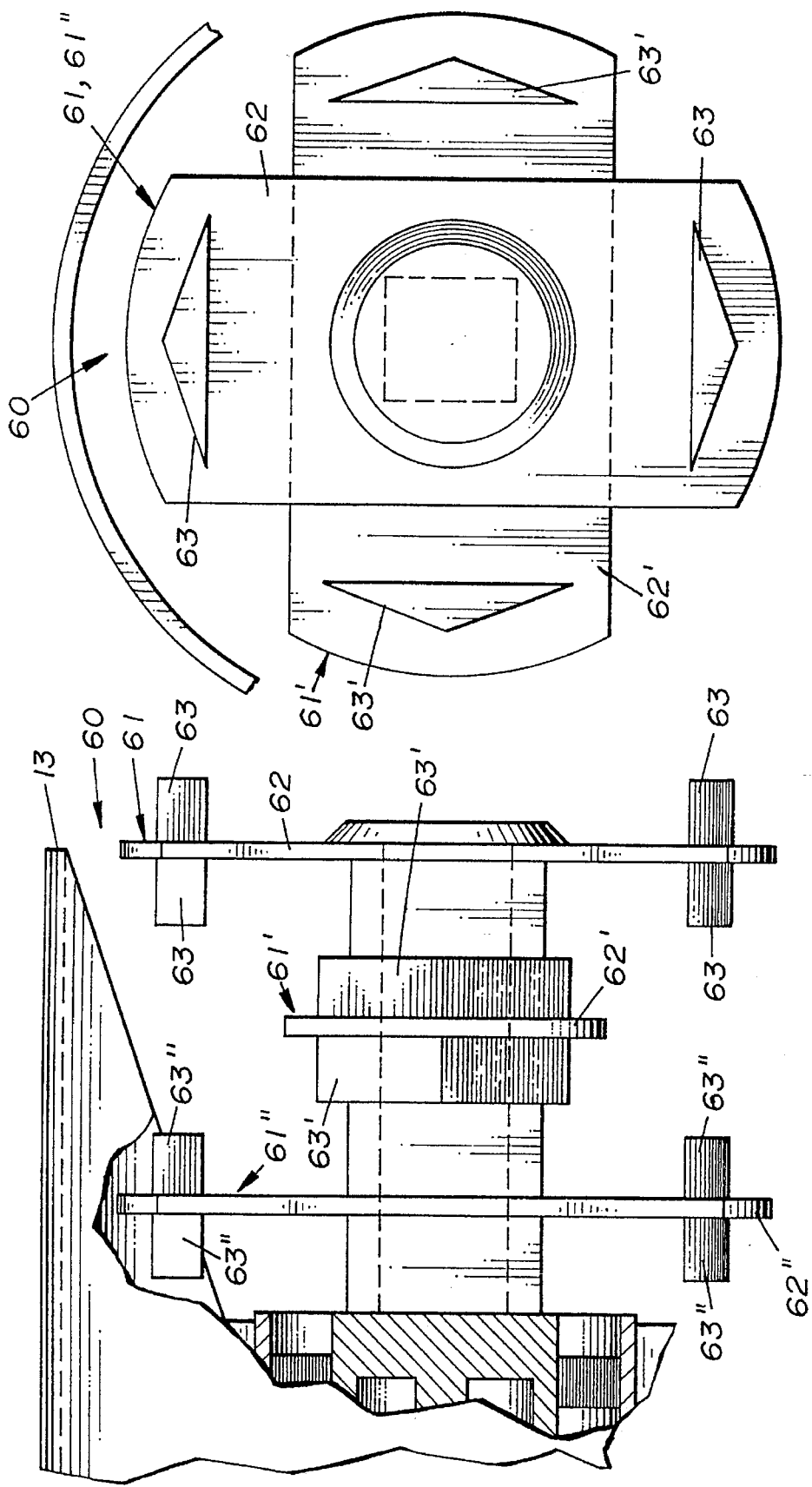

ROTATING CONSISTENCY TRANSMITTER AND METHOD

BACKGROUND OF THE INVENTION

1. Field of the Invention

The present invention is directed to a rotating torque measurement, and more specifically the use of a torque measurement to determine the consistency of a pulp slurry, the viscosity of a fuel oil, or in the mining industry, the concentration of a mining slurry in a grinding circuit.

2. Description of the Related Art

In the pulp and paper industry, the preparation and control of a pulp stream depends directly on the consistency of the moving pulp slurry. For example, the addition of bleaching additives, of retention aides, of various filler, starches and additives is all based on the consistency of pulp slurry. To date, the most accurate measurement of consistency is still based on a mechanical measurement of the shear forces exerted by the moving pulp stream on a sensing element.

Large boats and freighters are typically powered by large, oil-fired industrial boilers which use low grade, bunker fuel oils as the primary fuel. Bunker fuel oils are the residual grades of the petroleum distillation process and can have a very high viscosity. These types of fuel oils can only be injected into a boiler if they are pre-heated to sufficiently reduce their viscosity. The efficiency of the burning process directly depends on how well the bunker fuel oil can be made into a mist and how uniformly it can be injected into the boiler—both of these factors depend on the viscosity of the bunker fuel oil.

It has been found that both pulp consistency and fuel-oil viscosity can be determined by measuring the torque on the shaft of a rotating impeller. When consistency (or viscosity) increases, the shear forces on the rotating impeller increases and it takes a higher driving force (torque) to rotate the impeller. Commercial devices are available to affect such a measurement, such as a consistency transmitter type MEK-41 manufactured by BTG, a Swedish company, and a rotating viscosity meter manufactured by Brookfield, a USA company. The former device uses a sensing shaft concentrically mounted within a drive shaft. A shear force measuring element (impeller) is mounted on the exposed end of a "sensor shaft" which is positioned directly into the moving pulp stream or fuel-oil. The sensor shaft rotates with the same rotational velocity as the outer shaft and is loosely coupled thereto. The outer shaft provides the main rotational driving force to the impeller and shields the sensor shaft from the frictional forces between the drive shaft and the outer gasket material, which prevents the pulp slurry from entering the housing of the sensor unit.

In a typical implementation, the relative rotational motion between the inner sensor shaft and the outer drive shaft is sensed and a counter-torque is applied to the sensor shaft so that it will rotate at exactly the same rotational velocity as the drive shaft. This counter-torque is equal and opposite to the torque on the sensor shaft produced by the shear forces of the pulp slurry on the rotating impeller. In the prior art, this counter-torque is not based on an absolute measurement of torque, but rather on secondarily deduced factors as measured by an electronic transducer or a rotating pneumatic transducer operating on the flapper-nozzle principle.

While this technology has long been used and accepted by industry as the best and most accurate method of measuring consistency, it has two fatal draw-backs—lack of durability and reliability. A pulp slurry is very abrasive and corrosive. This means the gasket materials used to isolate the rotating shafts have a finite lifetime, measured in months, and when one of the gaskets fails, the entire device can fail catastrophically. Pulp slurry will then penetrate to the interior of the sensing housing and damage the sensitive elements. When a critical pulp consistency transmitter fails, the computerized process control loop goes out of control and the production line has to be shut down. For a large paper machine, the cost of such a forced shutdown is measured in the thousands of dollars per work shift. Therefore, it is important to provide a means to maintain and service a pulp consistency transmitter without having to shut down production.

Even though this invention makes specific reference to a pulp slurry and fuel oil, it should be understood that it also applies to a variety of other materials, such as natural and synthetic fibers like cotton, wool and kevlar fibers, as well as many other kinds of fluids, such as molasses in the crystallization process leading to the production of refined sugar.

SUMMARY OF THE INVENTION

It is, therefore, a general object of the present invention to provide an improved rotating consistency transmitter which is based on an absolute measurement of torque to allow for easy calibration both under laboratory as well as production conditions, and furthermore a device which incorporates certain features to make it very rugged for use in a corrosive and abrasive environment.

It is an object of the invention to provide such a transmitter which can be used, installed, serviced and dismounted without having to shut down a production line.

It is a further object of the invention to allow use of a transmitter which enables the measurement of torque to be linearized with increasing consistency.

It is a still further object of the invention to provide a method for accurately and predictably measuring the viscosity or consistency of a flowing multi-phase materials, such as a pulp slurry, in a pipeline.

These and other objects of the invention are met by providing a rotating consistency transmitter designed to measure the consistency, concentration or viscosity of a multi-phase material located in a container or flowing in a main pipeline by measuring the torque applied on a composite, torque detecting, rotating shaft. The rotating shaft comprises three concentrically aligned shafts—an outer drive shaft, a middle sensor shaft and an inner reference shaft. The three shafts are aligned and connected together so that when the outer drive shaft is rotated, the sensor shaft is rotated which, in turn, causes the reference shaft to rotate. In the preferred embodiment, the distal end of the outer drive shaft is attached to a rotating means capable of rotating the rotating shaft at a defined rotation speed. The proximal end of the reference shaft is connected to a force detecting means disposed inside the main pipeline. During operation when slurry is flowing through the main pipeline, rotation of the force detecting means is impeded thereby producing a twisting action on the sensor shaft. This twisting action produces a torque which is predictable and absolutely calibratable. The reference shaft, sensor shaft and drive shaft are isolated from the slurry.

Attached to the transmitter is a torque detecting means capable of detecting the amount of torque applied to the sensor shaft. In the preferred embodiment, the amount of torque is determined by measuring the angular displacement between the distal and proximal ends of the sensor shaft.

This angular displacement is measured by passing a focussed light beam across two closely aligned, transparent optical disks. Each optical disc has a plurality of opaque lines created thereon designed to prevent passage of light therethrough. One optical disk is attached to the distal end of the sensor shaft via the drive shaft while the other optical disk is attached to the distal end of the sensor shaft via the reference shaft. During operation, a focused beam of light is transmitted through the optical disks. The amount of light transmitted therethrough is a direct measurement of the torque acting on the sensor shaft.

As mentioned above, in one embodiment, the transmitter is attached to pipeline containing a flowing slurry. The transmitter is housed inside a carrying pipe which is selectively connected to the main pipeline via a positioning pipe. During assembly, the carrying pipe is inserted to the positioning pipe and attached thereto. An optional valve means is also provided which enables the positioning pipe to be selectively opened or closed thereby allowing the transmitter to be easily installed or removed from the main pipeline.

Using the above described transmitter, a method of measuring the consistency of a flowing liquid in a main pipeline is also provided.

BRIEF DESCRIPTION OF THE DRAWINGS

FIG. 6 is a side elevational view of a stacked, three-bladed impeller.

FIG. 7 is a front elevational view of the three-bladed impeller shown in FIG. 6.

DESCRIPTION OF THE PREFERRED EMBODIMENT(S)

The present invention in one embodiment finds preferred usage as a rotating consistency transmitter 2 in the pulp and paper industry. In a typical application in the bleach plant of a paper mill, the rotating consistency transmitter 2 is installed just prior to the chlorination stage, where the addition of chlorine to the pulp is critically controlled based on the amount of dry fiber flow. The amount of dry fiber flow is determined by the pulp flow velocity and the pulp consistency. The amount of chlorine added to the flowing pulp slurry determines how much the pulp gets bleached and also the residual amount of chlorine left after the bleaching stage. If the residual chlorine level is too high, this can lead to the formation of dioxin in the paper and also to the discharge of free chlorine into the atmosphere. Both conditions, of course, are undesirable.

Figure 1:
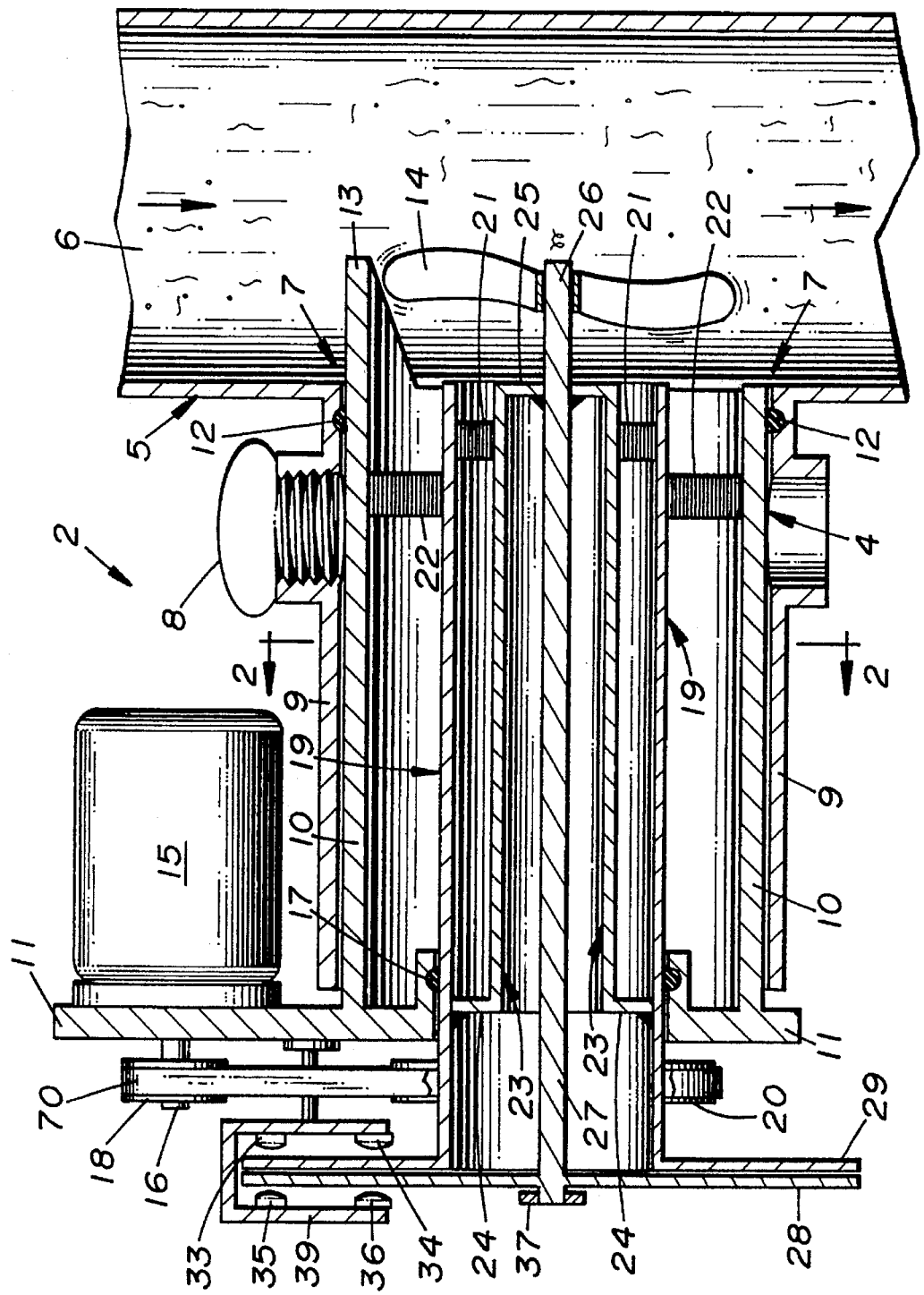
FIG. 1 is a sectional, side elevational view of the rotating consistency transmitter disclosed herein.

FIG. 1 shows the rotating consistency transmitter 2 comprising a carrying pipe 10 installed on the side of a main pipeline 5 which is transporting a pulp slurry 6 flowing in a downward direction. A side port 7 is formed on the side of the main pipeline 5 over which a positioning pipe 9 is attached. The longitudinal axis of the positioning pipe 9 is aligned perpendicularly with the longitudinal axis of the main pipeline 5 and is designed to hold a hollow, longitudinally aligned, snug-fitting, carrying pipe 10. An optional gate valve 8 may be attached to the positioning pipe 9 which enable the positioning pipe 9 to be selectively opened or closed.

Attached to the distal end of the carrying pipe 10 is a drive plate 11 designed to hold the rotating means. The drive plate 11 partially extends into the central area of the carrying pipe 10 thereby acting as a support and an alignment surface for the drive shaft 19. First and second O-ring seals 12, 17 are disposed between the positioning pipe 9 and the carrying pipe 10 to create a water-tight seal therebetween. Formed on the proximal end of the carrying pipe 10 is a lip structure 13 which extends into the main pipeline 5 and is designed to protect the rotating impeller 14 from the flowing pulp slurry 6.

In the preferred embodiment, the rotating means is a fractional horsepower motor 15 mounted to the drive plate 11. The motor's drive shaft 16 has a motor drive shaft sprocket 18 mounted thereon which, in turn, rotates a belt 70 and powers the large diameter sprocket 20. The large diameter sprocket 20 is directly connected to the distal end of the drive shaft 19. When the motor 15 is operated, the belt 70 turns the sprocket 20 which, in turn, rotates the drive shaft 19.

Longitudinally aligned and positioned inside the carrying pipe 19 is a sensor shaft 23. The sensor shaft 23 has a flange surface 24 formed at the distal end thereof and a closed end surface 25. The flange surface 24 is welded to the inside surface of the carrying pipe 19. The configuration provides a barrier to keep the slurry 6 from entering the electronic area adjacent to the transmitter 2.

Longitudinally aligned and positioned inside the sensor shaft 23 is a reference shaft 27. The distal end of the reference shaft 27 is attached to the first optical disk 28 discussed further below. The proximal end of the reference shaft 27 is welded and extends through the end surface 25 on the sensor shaft 23. A force detecting means, such as an impeller 14, is mounted to the portion 26 of the reference shaft 27 that extends into the main pipeline 6.

A first gasketed rotating seal 21 is positioned between the inside surface of the drive shaft 19 and the outside surface of the sensor shaft 23. A second gasketed rotating seal 22 is positioned between the outside surface of the drive shaft 19 and the inside surface of the carrying pipe 10. When slurry 6 is flowing in the main pipeline 5, the first and second seals 21, 22 prevent slurry 6 from getting between the sensor shaft 23 and the drive shaft 19 and between the drive shaft 19 and the carrying pipe 10, respectively.

It is important to note that while the first gasketed rotating seal 21 is stationary with respect to both the drive shaft 19 and the sensor shaft 23, the second gasketed rotating seal 22 is positioned between two surfaces, which are rotating with respect to each other. The whole reason for introducing the drive shaft 19 is to prevent the frictional forces between the rotating drive shaft 19 and the stationary carrying pipe 10 from influencing the torque measurement across the sensor shaft 23. All frictional forces are taken up by the second seal 22 and are decoupled from the operation of the sensor shaft 23.

As mentioned above, the sensor shaft 23 is welded at its distal end to the inside surface of the drive shaft 19. During operation, shear forces acting on the impeller 14 causes a torque to act over the whole length of the sensor shaft 23, which produces a slight twisting action thereon. This twisting action is monitored by a reference shaft 27 which is welded to the inside surface of the proximal end of the sensor shaft 23. By fastening one first disk 28 to the distal end of the reference shaft 27 and a second disk 29 to the distal end of the drive shaft 19, respectively, one can directly observe the twist over the full length of the sensor shaft 23. In particular, it should be noted that the extent of the twisting action is a direct measure of the torque acting on the sensor shaft 23 and is an absolute quantity that can be directly related to the physical parameters of the sensor shaft 23, (i.e. the length, inner and outer diameters, material of construction, and its modulus of rigidity).

The relationship between torque and twisting action can not only be expressed in concise mathematical terms but also by a straightforward empirical measurement, e.g. by holding one end of the sensor shaft 23 rigid, while applying a known amount of torque to the opposite end. This procedure can be easily repeated for different shafts to check the response of each shaft to a known amount of torque. In other words, if one holds the physical parameters of the sensor shaft 23 within tight specifications, one is able to measure the applied torque in absolute terms simply by measuring the amount of twisting action on the sensor shaft 23.

As shown in FIG. 1, the first and second optical disks 28, 29 are mounted to the ends of the reference shaft 27 and drive shaft 19, respectively. Two focussed laser diodes 33, 34 are radially mounted on a converted, U-shaped bracket 39 disposed over the peripheral edges of the disks 28, 29. The diodes 33, 34 are mounted on the bracket 39 along one side of the first and second optical disks 28, 29. Two respective light sensing photo diodes 35 36 are mounted radially on the opposite side of the bracket 39 on the opposite side of the optical disks 28, 29. A mounting nut 37 is used to fasten the first optical disk 28 to the end of the reference shaft 27.

Figures 2, 3:
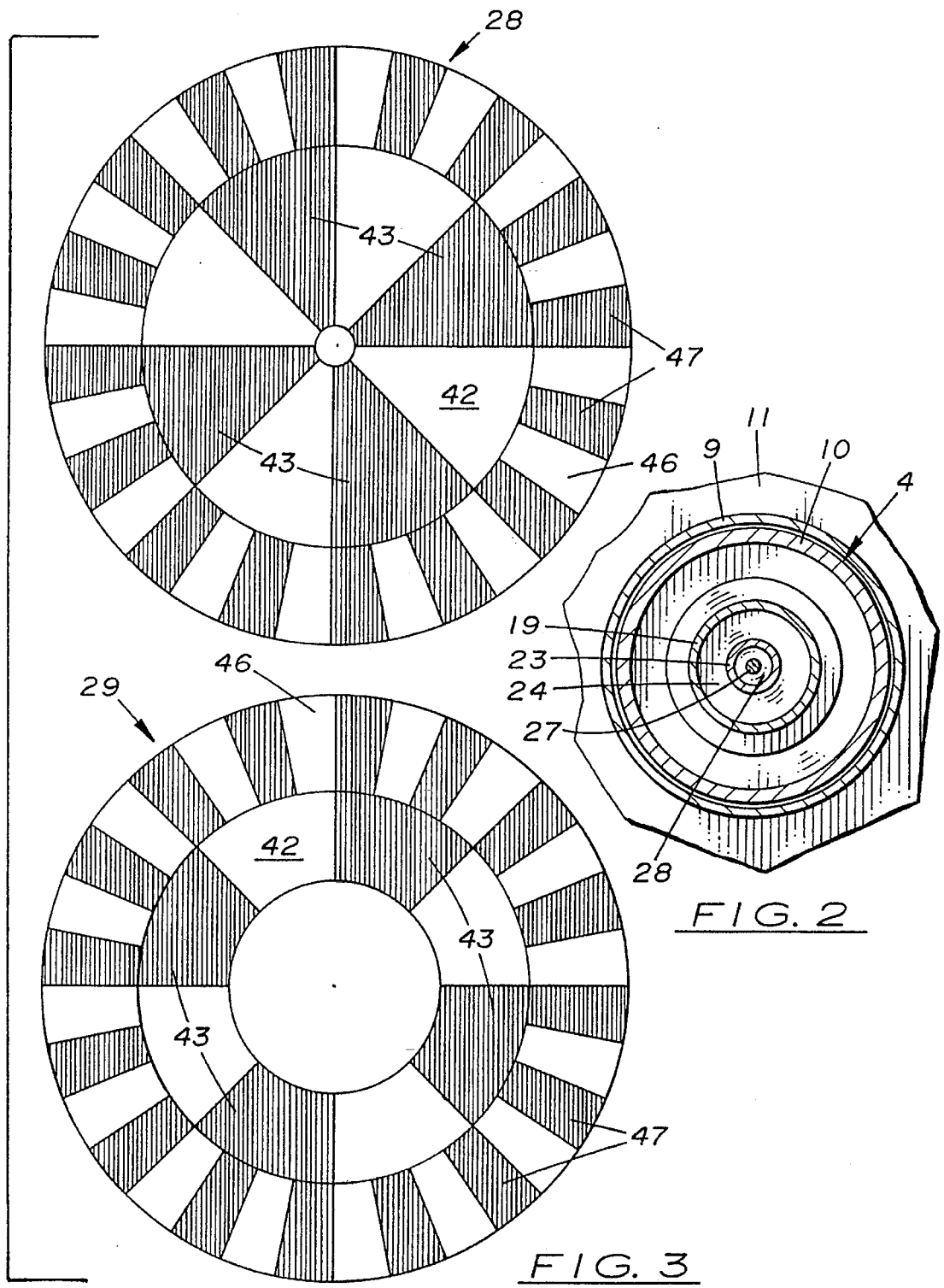
FIG. 2 is a sectional, front elevational view taken along Line 2—2 in FIG. 1.
FIG. 3 is a front plan view of the first and second disks.
Figure 4:
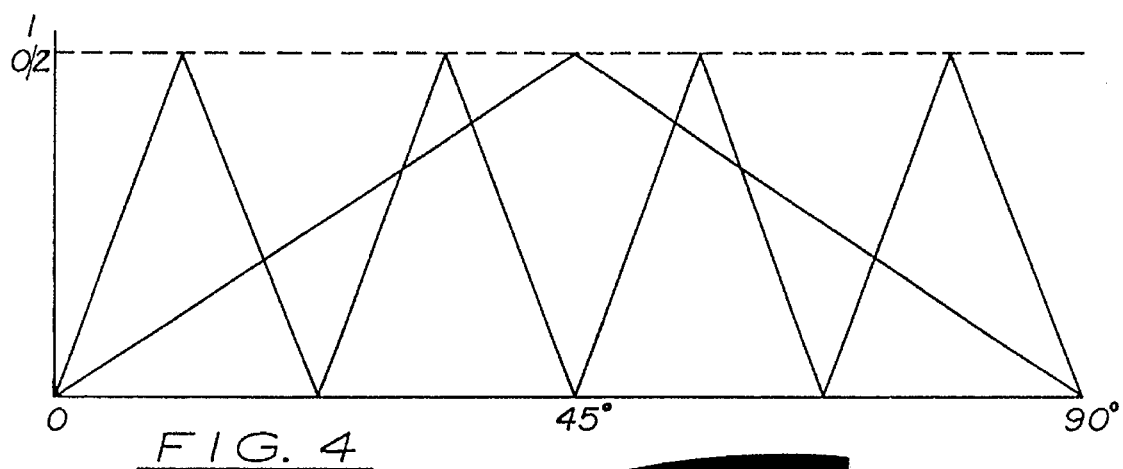
FIG. 4 is a diagram showing the relationship between the amount of light transmitted across the two optical disks and the amount of angular displacement.

FIG. 3 is a front elevation view of the two complementary first and second optical disks 28, 29, respectively. Optical disks 28, 29 are made of rigid, transparent material, such as glass or acrylic material with an inner circle area 42 having four opaque lines 43 and an outer circle area 46 having sixteen opaque lines 47. When initially installed on the transmitter 2, the positions of the optical disks 28, 29 are adjusted so that no light is transmitted across the two-disk interface. Then, when a torque is applied to the sensor shaft 23, the first and second optical disks 28, 29 are displaced with respect to the other, thereby allowing a certain amount of light to be transmitted in direct proportion to the amount of angular displacement of one disk with respect to the other. The maximum transmitted light intensity is 0.5 $I_o$, where $I_o$ is the full light output from the laser diode. This effect is linear up to a certain angular displacement, which depends on the number of lines on the disk's inner and outer circle areas 42, 46, respectively. Using this embodiment, the amount of light transmitted across the two optical disks, shown in FIG. 4, will be linear and will reach the maximum value (of $I_o/2$) for a displacement of 45° for the inner circle area 42 and 11.25° for the outer circle area 46. The corresponding amount of transmitted light is shown in FIG. 4 as a function of angular displacement. Obviously, by adding more opaque lines, one can increase the accuracy of this measurement.

Figure 5:
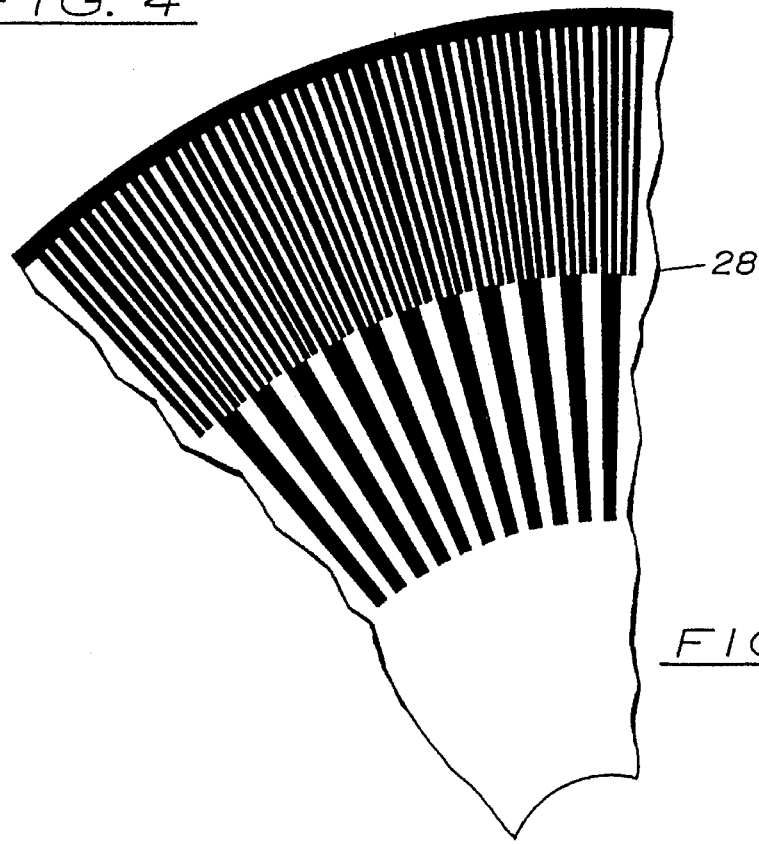
FIG. 5 is a front plan view of an optical disk with a high density of opaque lines manufactured thereon.

With high resolution photo-etching techniques, it is possible to create many more lines on the optical disks as shown in FIG. 5. Let us assume a line density for the outer pattern of one line per degree or a full range of light transmission from 0 to $I_o/2$, over 0.5 degree of angular displacement.

Let us assume we use 360 optical lines per revolution, i.e. 1 line per 1° of angular displacement, then for an optical disk of 7.5 cm (3") diameter, the thickness of each line is equivalent to 0.5°, or about 16 micron in width. This means if we use a laser diode focussed down at the plane of the optical disk to produce a line measuring 33 microns (in width) by 2,000 microns (in length—aligned radially parallel to the lines) one can accurately measure the amount of rotational displacement (of one disk with respect to the other) to a resolution of better than 0.01°.

Let us further assume that the sensor shaft 23 is 20 inches long with an outer diameter of 12.7 mm (0.5 inches) and a wall thickness of 0.89 mm (0.035 inches). Then one can exactly calculate the amount of angular displacement "q" for a maximum amount of torque T as follows:

$q = (32\ T\ L) / (3.14\ (D_o^4 - D_i^4)G)$, measured in radians, where:

T=torque=13 inch-pounds max
L=length of the sensor shaft=20 inches
$D_o$=outer diameter of the sensor shaft=0.5 inches
$D_i$=inner diameter of the sensor shaft=0.43 inches and,
G=modulus of rigidity of titanium=$5.6 \times 10^6$ psi. With these parameters, using type II titanium alloy and a torque of 13 inch—pounds, the maximum amount of angular displacement is 0.034 radians, or about 2°. The beauty of this type of measurement is that it is an absolute measurement of torque and only depends on the dimensions and the material of the shaft, i.e. the modulus of rigidity of the titanium shaft of the specific dimensions. The angular displacement of the sensor shaft 23 can be accurately calculated and even more accurately measured using static measuring techniques. Another important advantage of this type of configuration is that (i) the structural integrity of the concentric shafts 19, 23, 27 is fully preserved, and (ii) there is no relative free motion between the outer and inner shafts 19, 27, respectively. These are two important benefits over the technology commonly used today, where the survivability of the whole system depends on the integrity of the first rotating seal 21 between the drive shaft 19 and the sensor shaft 23. In the prior art, a break in this seal 21 leads to the catastrophic failure of the whole system, whereas in the herein described invention, a break in the seal 21 merely allows some of the slurry 6 to leak between the sensor shaft 23 and the drive shaft 19. As there is no relative motion between the two shafts 19, 23, the effect of a leak has a negligible effect on the measurement.

Referring back to FIG. 1, it should be noted that the configuration of the positioning pipe 9 is such that it allows the impeller 14 to be pulled back out of the slurry stream far enough to be extracted past the gate valve 8. Once the impeller 14 clears the gate valve 8, the gate valve 8 can be shut, thereby allowing the rotating consistency transmitter 2 to be removed from the positioning pipe 9 without having to shut down the production line. This is an important advantage in cases where it is important to maintain a constant production cycle.

Kerekes et. al. (Ref.: *Motion of Pulp Fibre Suspensions in Rotary Devices*, C. P. J. Bennington, R. J. Kerekes, and J. R. Grace, The Canadian Journal of Chemical Engineering, Vol. 69, February 1991, page 251–258) have shown that, to a first order approximation the torque resulting from the shear forces of a pulp slurry acting on a rotating impeller has a relationship that is somewhere between a square law and a cube law with consistency. This means that for higher consistencies, above 8%, the shear forces are so high that even with a relatively small impeller, with a 3.5" diameter, the torque can easily be measured. However, at smaller consistencies, below 3%, the shear forces are relatively small. With the above-described gate-valve 8 configuration, the maximum diameter of the impeller is determined by the maximum opening size of the gate valve 8.

FIGS. 6 and 7 show another embodiment of the force detecting means including a stacked, three bladed impeller 60. The impeller 60 has three blades 61, 61', and 61" stacked side by side each other with each successive impeller being rotated 90°, so that the slurry can flow freely between the neighboring blades. Each blade 61, 61', 61" comprises a thin, rectangular-shaped plate 62, 62' 62", respectively, with two pairs of separating wings 63, 63', 63" at each side of the plate at opposite ends. A square-shaped mounting hole is also provided which enables the impeller 60 to fit onto a complementary shaped reference shaft.

FIGS. 1 and 5 show an optional flow breaker lip structure 13 located at the end of the carrying pipe 10. This lip structure 13 breaks up the pulp flow in front of the impeller(s) and reduces the influence of the velocity of the pulp slurry 6. It also protects the impeller 14 from the impact of dried pulp slugs, which can destructively impact anything positioned inside the flow line. The size and shape of this lip structure 13 depends on the consistency of the pulp flow and the number of impeller blades. In some instances, it may in fact be preferable to mount the lip structure 13 some distance upstream from the impeller 14 in order to minimize the amount of dewatering of the pulp prior to the measuring region, which could give erroneous readings of consistency.

According to the Handbook of Chemistry and Physics (published by: The Chemical Rubber Publishing Co., 1961, page 2194) the viscosity of a substance is defined as "the tangential force per unit area of either of two horizontal planes at unit distance apart, one of which is fixed, while the other moves with unit velocity, the space being filled with the substance."

Figure 8:
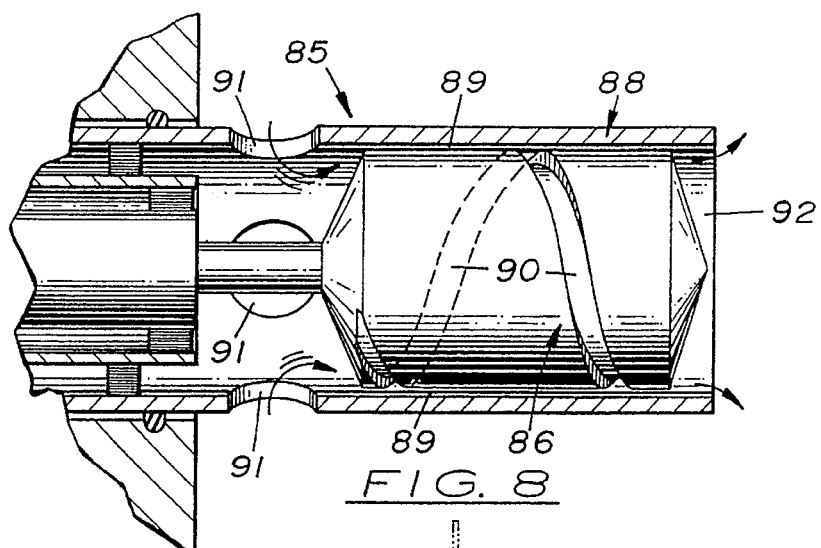
FIG. 8 is a side elevational view of the rotary viscosimeter.

FIG. 8 shows still another embodiment of the force detecting means comprising a rotary viscosimeter 85. The viscosimeter 85 is similar to the viscosimeter disclosed by Winter in U.S. Pat. No. 4,077,251 having an inner cylindrical shape 86 which rotates within a larger outside cylinder 88. The gap 89 between the cylindrical shape 86 and the cylinder 88 is constant. The cylindrical shape 86 and the cylinder 88 define the two horizontal planes, and the torque which has to be applied to the inner rotating cylinder 86 defines the tangential force referred to in the above-referenced definition. A narrow screw band 90 is attached to the outer surface of the cylindrical shape 86 to draw fluid in through holes 91 located in the outer cylinder 88 along the gap 89 and out through the opening 92 on the cylinder 88 back into the primary flow. This ensures that the fluid substance within the cylindrical shape 86 and the cylinder 88 is continually being exchanged.

To linearize the measurement of consistencies ($C_y$) over a wide range of readings, it is necessary to apply a fractional root function to the raw torque reading (t), as follows:

$$C_y = a \, t^{-1/b}$$

where "a" is a constant and "b" is a factor between 2 and 3. In the simplest form, "b" is 2, and the consistency is simply obtained by using a square root conversion circuit using an 'integrated circuit multiplier' type AD532 from Analog Devices, or similar (ref.: 1992 Special Linear Reference Manual, published by Analog Devices). The same device can also be used to obtain a cube root function or various combinations in between.

Figure 9:
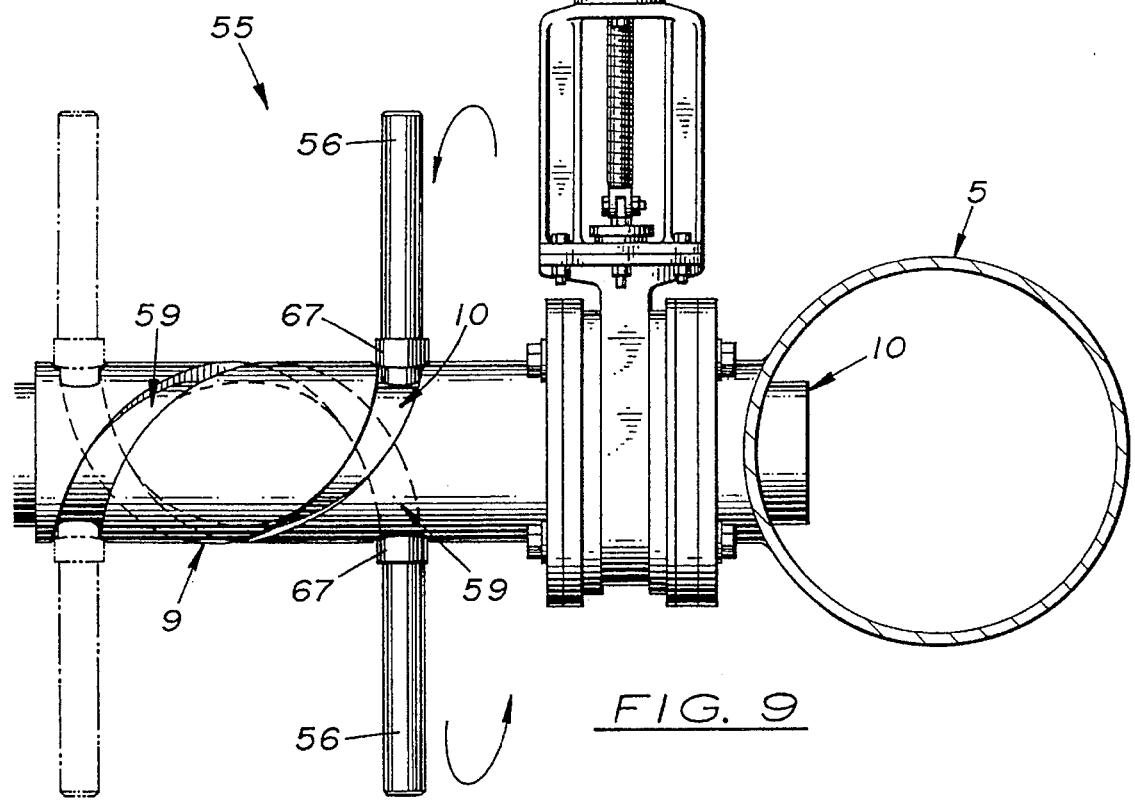
FIG. 9 is a side elevational view of the extraction device which allows the impeller to be extracted past the gate valve.

FIG. 9 shows a screw feed leveraging device 55 to allow the rotating consistency transmitter 2 to be safely removed from the in-line position in the positioning pipe 9 to an extracted position. It should be noted that some main pipelines can operate up to a pressure of 10 bar, i.e. 150 psi. At 3.5 inch diameter, the cross-sectional area of such pipelines is 9.62 square inches, which, at 10 bar, results in a total pressure of 1,440 pounds of force. In the embodiment shown, the leveraging device 55 includes two 6-inch long handles 56, 57 threadingly attached at one end to the opposite sides of the carrying pipe 10. The two handles 56, 57 extend through a cork-screw cut-out 59 located on the positioning pipe 9. The handles 56, 57 are then used both as a leveraging tool and as positioning tool to allow the impeller 14 to be safely pulled back from its extended position in the pulp slurry 6.

Using the above described transmitter 2, a method for measuring the consistency of a flowing liquid in a pipeline is also disclosed. The method comprises the following steps:

a. selecting a consistency transmitter disclosed herein;

b. locating the consistency transmitter so that the force detecting means is placed into the slurry;

c. rotating said force detecting means in said slurry;

d. measuring the amount of light transmitted across said first and second optical disks;

e. determining the amount of torque across said sensor shaft based on the amount of light transmitted across said first and second optical disks; and, f. calculating the consistency of said slurry based on the torque measurement on said sensor shaft.

In compliance with the statute, the invention, described herein, has been described in language more or less specific as to structural features. It should be understood, however, the invention is not limited to the specific features shown, since the means and construction shown comprised only the preferred embodiments for putting the invention into effect. The invention is, therefore, claimed in any of its forms or modifications within the legitimate and valid scope of the amended claims, appropriately interpreted in accordance with the doctrine of equivalents.

We claim:

1. A consistency transmitter, comprising:

a. a composite, rotating shaft including concentrically aligned outer drive shaft, a middle sensor shaft, and an inner reference shaft, said shafts being connected together so that when said outer drive shaft is rotated, said sensor shaft is rotated and causes said reference shaft to rotate, said reference shaft having an extended end;

b. a force detecting means attached to said extended end of said reference shaft;

c. a torque detecting means connected between said outer drive shaft and said inner reference shaft, said torque detecting means capable of detecting the amount of torque applied across to said sensor shaft; and, d. a rotating means attached to said outer drive shaft for rotating said force detecting means.

2. A consistency transmitter as recited in claim 1, wherein said torque detecting means comprises a two optical disks, a light generating means, and light detecting means, each said optical disk having a plurality of opaque lines formed thereon capable of preventing the transmission of light therethrough, said optical disks being aligned in side by side manner with one said optical disk being attached to said outer drive shaft and other said optical disk being attached to said reference shaft, said light generating means and said light detecting means being disposed on opposite sides of said optical disks aligned in a side by side manner to measure the amount of light transmitted through said optical disks.

3. A consistency transmitter as recited in claim 1, wherein said force detecting means is an impeller.

4. A consistency transmitter as recited in claim 1, wherein said force detecting means is an stacked impeller.

5. A consistency transmitter as recited in claim 1, wherein said force detecting means is a partially enclosed, grooved cylinder.

6. A consistency transmitter as recited in claim 1, further including a connecting means for attaching said transmitter to a main pipeline, said connecting means includes a hollow positioning pipe attached to said main pipeline and a hollow carrying pipe capable of being inserted into said positioning pipe.

7. A consistency transmitter as recited in claim 6, further including a gate valve disposed on said positioning pipe enabling said positioning pipe to selectively be opened and closed to enable the insertion or removal of said force detecting means from said main pipeline.

8. A consistency transmitter as recited in claim 7, further including a leveraging device enabling said carrying pipe to be easily removed from said carrying pipe.

9. A consistency transmitter as recited in claim 6, further including a first sealing means disposed between said carrying pipe and said outer drive shaft to provide a water-tight seal therebetween.

10. A consistency transmitter for a slurry flowing in a main pipeline, comprising:

a. a carrying pipe attached to the main pipeline;
   b. a rotating shaft longitudinally aligned and disposed inside a carrying pipe, said rotating shaft including concentrically aligned outer drive shaft, middle sensor shaft and an inner reference shaft, said shafts being connected together so that when said outer shaft is rotated, said sensor shaft is rotated and causes said reference shaft to rotate, said reference shaft having an extended end disposed inside said main pipeline;
   c. a force detecting means attached to said extended end of said reference shaft;
   d. a torque detecting means attached to said rotating shaft capable of detecting the amount of torque applied to said rotating shaft, said torque detecting means includes two optical disks, a light generating means, and light detecting means, each said disk having a plurality of opaque lines formed thereon capable of preventing the transmission of light therethrough, said optical disks being aligned in side by side manner with one said optical disk being attached to the proximal end of said outer shaft and said second optical disk being attached to the proximal end of said reference shaft, said light generating means being attached to said transmitter and capable of transmitting a light beam through said optical disks, said light detecting means being attached to said transmitter and capable of detecting said light transmitted through said optical disks from said light generating means.
   e. a rotating means for rotating said outer drive shaft; and,
   f. connecting means for connecting said transmitter to the main pipeline, said connecting means includes a hollow positioning pipe attached to said main pipeline and a hollow carrying pipe, said rotating shaft being longitudinally aligned and placed inside said carrying pipe and said carrying pipe being longitudinally aligned and placed inside said positioning pipe to connect said transmitter to said main pipeline.

11. A consistency transmitter as recited in claim 10, further including a gate valve disposed on said positioning pipe enabling said positioning pipe to selectively opened and closed to enable the insertion or removal of said force detecting means from said main pipeline.

12. A consistency transmitter as recited in claim 11, further including a leveraging device for holding said carrying pipe in said positioning pipe.

13. A consistency transmitter as recited in claim 12, wherein said leveraging device is a pair of locking handles attached to said carrying pipe enabling said carrying pipe to be pulled back in said positioning pipe.

14. A consistency transmitter as recited in claim 12, wherein said force detecting means is an impeller.

15. A consistency transmitter as recited in claim 14, further including a lip structure which extends into said main pipeline to impede the flow of slurry against said impeller.

16. A consistency transmitter as recited in claim 12, wherein said force detecting means is an stacked impeller.

17. A consistency transmitter as recited in claim 12, wherein said force detecting means is a partially enclosed, grooved cylinder.

18. A method for measuring the consistency of a slurry, comprising the following steps:

a. selecting a consistency transmitter which includes a composite, rotating shaft including concentrically aligned outer drive shaft, a middle sensor shaft, and an inner reference shaft, said shafts being connected together so that when said outer drive shaft is rotated, said sensor shaft is rotated and causes said reference shaft to rotate, said reference shaft having a proximal end, a force detecting means attached to said proximal end of said reference shaft, a torque detecting means connected between said outer drive shaft and said inner reference shaft, said torque detecting means capable of detecting the amount of torque applied across to said sensor shaft, and a rotating means attached to said outer drive shaft for rotating said force detecting means;
   b. placing said consistency transmitter so that said force detecting means is disposed in said slurry;
   c. rotating said force detecting means in said slurry;
   d. determining the amount of torque across said sensor shaft using said torque detecting means; and,
   e. calculating the consistency of said slurry based on the torque measurement on said sensor shaft.

19. A method for measuring the consistency of a slurry as recited in claim 18 wherein said step (f) of calculating the consistency of said slurry using a fractional root function correction circuit.

\* \* \* \* \*